United States Patent
Luo et al.

(10) Patent No.: US 11,950,888 B2
(45) Date of Patent: Apr. 9, 2024

(54) PULSE DIAGNOSTIC DEVICE AND SYSTEM OF PULSE DIAGNOSIS

(71) Applicant: SHENZHEN TATFOOK WISDOM HEALTH TECHNOLOGY CO., LTD., Shenzhen (CN)

(72) Inventors: Yu Luo, Shenzhen (CN); Tiecai Li, Shenzhen (CN); Xianrui Liang, Shenzhen (CN); Tong Zhang, Shenzhen (CN); Jianhao Liu, Shenzhen (CN); Libao Zhang, Shenzhen (CN); Yating Li, Shenzhen (CN)

(73) Assignee: SHENZHEN TATFOOK WISDOM HEALTH TECHNOLOGY CO., LTD., Shenzhen (CN)

( * ) Notice: Subject to any disclaimer, the term of this patent is extended or adjusted under 35 U.S.C. 154(b) by 861 days.

(21) Appl. No.: 16/931,410

(22) Filed: Jul. 16, 2020

(65) Prior Publication Data
US 2020/0345249 A1    Nov. 5, 2020

Related U.S. Application Data

(63) Continuation of application No. PCT/CN2018/087892, filed on May 22, 2018.

(51) Int. Cl.
*A61B 5/021* (2006.01)
*A61B 5/00* (2006.01)
*A61B 5/0235* (2006.01)

(52) U.S. Cl.
CPC ........ *A61B 5/02141* (2013.01); *A61B 5/0004* (2013.01); *A61B 5/0235* (2013.01); *A61B 2562/0247* (2013.01)

(58) Field of Classification Search
None
See application file for complete search history.

(56) References Cited

U.S. PATENT DOCUMENTS 6,168,567 B1 * 1/2001 Pickering ............... A61B 5/742
   600/490
8,211,030 B2   7/2012 Donehoo et al.
(Continued)

FOREIGN PATENT DOCUMENTS

CN   1608584 A   4/2005
CN   1778269 A   5/2006
(Continued)

OTHER PUBLICATIONS

Chinese First Office Action, Chinese application No. 201880041266.7, dated Dec. 15, 2021 (26 pages).
(Continued)

*Primary Examiner* — Devin B Henson
*Assistant Examiner* — Matthew Eric Ogles

(57) ABSTRACT

A pulse diagnostic device and a system of pulse diagnosis are provided. The pulse diagnostic device includes a cuff and a main monitor. The cuff includes a tube and an air bag arranged with an air path interface. A gas medium is received in the air bag. The tube is connected to the air path interface. The main monitor includes a pressure sensor and a controller. The tube extends to reach the main monitor and is connected to the pressure sensor, and the pressure sensor further connects to the controller. When the pulse diagnostic device is working, the cuff contacts an artery, the pressure sensor senses a pressure of the gas medium in the tube. The pressure sensor transmits the pressure of the gas medium to the controller. The controller obtains the pulse information and the blood pressure information based on the pressure of the gas medium.

13 Claims, 5 Drawing Sheets

(56) References Cited

U.S. PATENT DOCUMENTS

| | | | |
|---|---|---|---|
| 2002/0147401 A1* | 10/2002 | Oka | A61B 5/02125 |
| | | | 600/490 |
| 2004/0059232 A1 | 3/2004 | Narimatsu | |
| 2005/0119578 A1 | 6/2005 | Kubo | |
| 2009/0036786 A1* | 2/2009 | Gough | A61B 5/022 |
| | | | 600/492 |
| 2010/0241013 A1* | 9/2010 | Hatib | A61B 5/0215 |
| | | | 600/485 |
| 2012/0330112 A1* | 12/2012 | Lamego | A61B 5/7225 |
| | | | 600/483 |
| 2013/0226012 A1 | 8/2013 | Kinoshita | |
| 2019/0357783 A1* | 11/2019 | Tawara | A61B 5/02208 |

FOREIGN PATENT DOCUMENTS

| | | |
|---|---|---|
| CN | 101006913 A | 8/2007 |
| CN | 101077299 A | 11/2007 |
| CN | 101112308 A | 1/2008 |
| CN | 101579235 A | 11/2009 |
| CN | 201617821 U | 11/2010 |
| CN | 201641987 U | 11/2010 |
| CN | 102293642 A | 12/2011 |
| CN | 202198587 U | 4/2012 |
| CN | 102579023 A | 7/2012 |
| CN | 202505340 U | 10/2012 |
| CN | 102885619 A | 1/2013 |
| CN | 202920160 U | 5/2013 |
| CN | 203195664 U | 9/2013 |
| CN | 103654727 A | 3/2014 |
| CN | 203883964 | 10/2014 |
| CN | 104382569 A | 3/2015 |
| CN | 204909410 U | 12/2015 |
| CN | 105769158 A * | 7/2016 |
| CN | 106236057 A | 12/2016 |
| CN | 107440694 A | 12/2017 |

OTHER PUBLICATIONS

International Search Report and Written Opinion for related International application No. PCT/CN2018/087892, dated Feb. 25, 2019 (8 pages).

Chinese Second office action, Chinese application No. 201880041266.7, dated Aug. 23, 2022 (26 pages).

Chinese Rejection decision, Application No. 201880041266.7, dated Dec. 28, 2022 (21 pages).

* cited by examiner

PULSE DIAGNOSTIC DEVICE AND SYSTEM OF PULSE DIAGNOSIS

CROSS-REFERENCE TO RELATED APPLICATIONS

The present application is a continuation-application of International (PCT) Patent Application No. PCT/CN2018/087892 filed on May 22, 2018, the entire contents of which are hereby incorporated by reference in its entirety.

TECHNICAL FIELD

The present disclosure relates to the field of traditional Chinese medical science, and in particular to a pulse diagnostic device and a system of pulse diagnosis.

BACKGROUND

Pulse diagnosis is one of four types of diagnosis in traditional Chinese medicine and is a unique diagnostic method. A finger may be used to sense and analyze characteristics of a pulse, such as a position at which the pulse is shown, a pulse rate, a width of the pulse, a trend of the pulse, and the like. A function and a state of an organ may be determined based on the characteristics of the pulse, such that non-invasive diagnosis may be achieved, providing a positive meaning for diagnosing and treating diseases.

Currently, a pulse diagnostic device in the market may be able to sense and understand a process of pulse diagnosis, and the pulse may be transferred into a graph and digitalized. A pulse wave may be a physical presence of the pulse of traditional Chinese medicine. The pulse wave may include and imply all information of the pulse. The pulse may be acknowledged directly and apparently via a graphic pulse wave, providing an instruction for diagnosis.

In a long-term study, the applicant of the present disclosure discovers that the pulse diagnostic device in the market may have a single function to obtain pulse information of an artery of a user only.

SUMMARY OF THE DISCLOSURE

According to a first aspect of the present disclosure, a pulse diagnostic device may be provided and include: a cuff and a main monitor. The cuff includes a tube and an air bag. The air bag is arranged with an air path interface, the air bag defines a chamber capable of receiving a gas medium, the tube is connected to the air path interface, and the tube defines a channel communicating with the chamber of the air bag. The main monitor includes a pressure sensor and a controller. The tube extends to reach the main monitor and is connected to the pressure sensor, and the pressure sensor is further connected to the controller. The cuff is configured to contact an artery of a user, the pressure sensor is configured to sense a pressure of the gas medium in the tube, the pressure sensor is configured to transmit the sensed pressure of the gas medium to the controller, and the controller is configured to obtain pulse information and blood pressure information of the user based on the pressure of the gas medium.

According to a second aspect of the present disclosure, a system of pulse diagnosis is provided and includes a pulse diagnostic device and a mobile terminal. The pulse diagnostic device includes: a cuff, a main monitor, and a communication assembly. The cuff includes a tube and an air bag. The air bag is arranged with an air path interface, the air bag defines a chamber capable of receiving a gas medium, the tube is connected to the air path interface, and the tube defines a channel communicating with the chamber of the air bag. The main monitor includes: a pressure sensor and a controller. The tube extends to reach the main monitor and is connected to the pressure sensor, and the pressure sensor is further connected to the controller. The cuff is configured to contact an artery of a user. The pressure sensor is configured to sense a pressure of the gas medium in the tube. The pressure sensor is configured to transmit the sensed pressure of the gas medium to the controller. The controller is configured to obtain pulse information and blood pressure information of the user based on the pressure of the gas medium. The communication assembly is configured to transmit the pulse information and blood pressure information to the mobile terminal.

According to a third aspect of the present disclosure, a system of pulse diagnosis is provided and includes a pulse diagnostic device and a server. The pulse diagnostic device includes: a cuff, a main monitor, and a communication assembly. The cuff includes a tube and an air bag. The air bag is arranged with an air path interface, the air bag defines a chamber capable of receiving a gas medium, the tube is connected to the air path interface, and the tube defines a channel communicating with the chamber of the air bag. The main monitor includes: a pressure sensor and a controller. The tube extends to reach the main monitor and is connected to the pressure sensor, and the pressure sensor is further connected to the controller. The cuff is configured to contact an artery of a user. The pressure sensor is configured to sense a pressure of the gas medium in the tube and transmit the sensed pressure of the gas medium to the controller. The controller is configured to obtain pulse information and blood pressure information of the user based on the pressure of the gas medium. The communication assembly is configured to transmit the pulse information and blood pressure information to the server. The server is configured to receive the pulse information and the blood pressure information, evaluate health of the user based on the pulse information and the blood pressure information, and send an evaluation result to the pulse diagnostic device, and the pulse diagnostic device is configured to display the evaluation result.

BRIEF DESCRIPTION OF THE DRAWINGS

To further illustrate technical solutions of embodiments of the present disclosure more clearly, drawings for the embodiments will be briefly described hereinafter. Obviously, the drawings described in the following are some embodiments of the present disclosure. Any skilled in the art can obtain other drawings based on the following drawings without any creative work.

DETAILED DESCRIPTION

Technical solutions of the present disclosure will be illustrated clearly and comprehensively by referring to drawings of embodiments of the present disclosure. Obviously, embodiments to be described are only a part of, but not all of, the embodiments of the present disclosure. Based on the embodiments of the present disclosure, other embodiments obtained by any skilled in the art without making creative work should be within the scope of the present disclosure.

Figure 1:
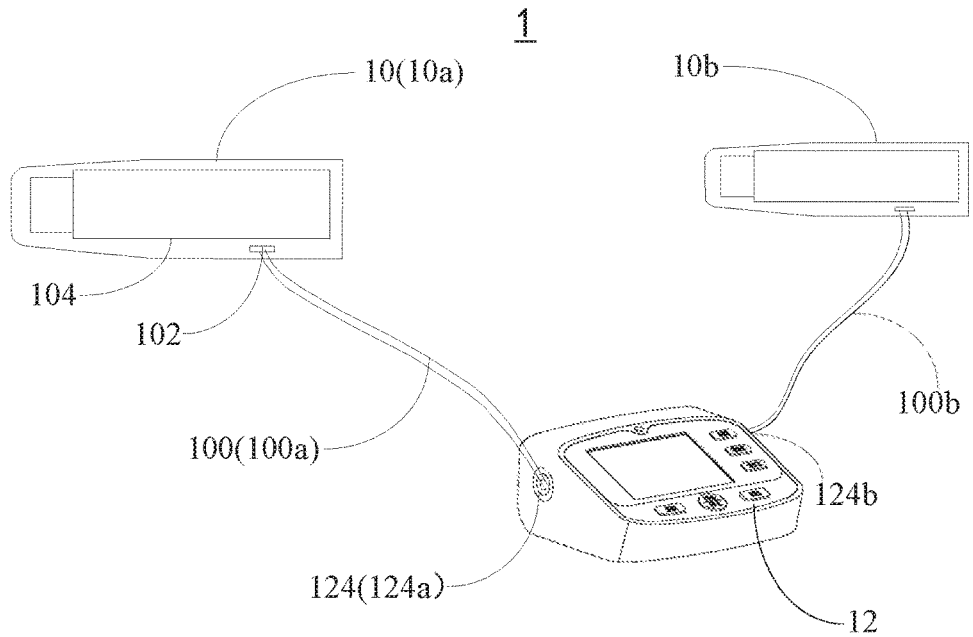
FIG. 1 is a structural schematic view of a pulse diagnostic device according to an embodiment of the present disclosure.
Figure 2:
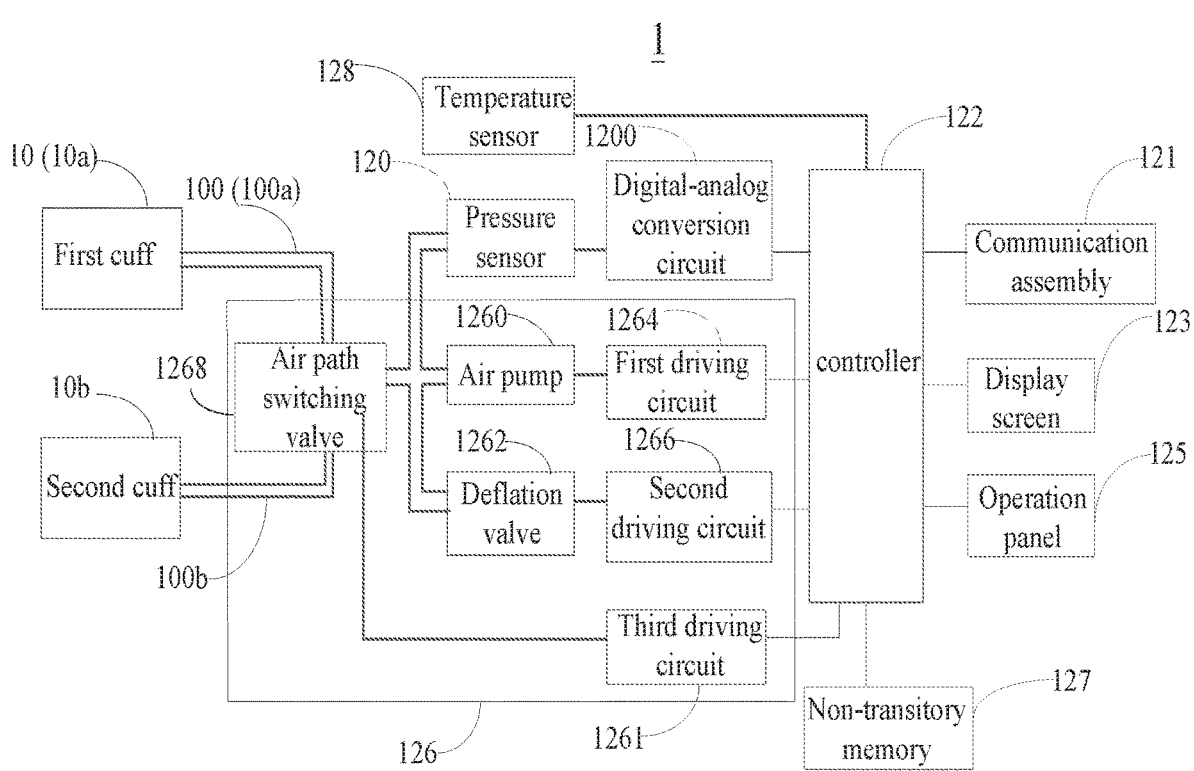
FIG. 2 is a structural diagram of hardware of the pulse diagnostic device shown in FIG. 1.

As shown in FIG. 1 and FIG. 2, a structural schematic view of a pulse diagnostic device is shown in FIG. 1, and a structural schematic view of hardware of the pulse diagnostic device shown in FIG. 1 is shown in FIG. 2. The pulse diagnostic device shown in FIG. 1 includes a cuff 10 and a main monitor 12.

To be specific, the cuff 10 may include a tube 100 and an air bag 104. The air bag 104 may be arranged with an air path interface 102. The air bag 104 may define a chamber, and a gas medium (such as air and the like) may be received in the air bag 104. The tube 100 may define a channel, and the gas channel may communicate with the chamber of the air bag 104. The gas medium may flow between the channel of the tube 100 and the chamber of the gas bag 104. The tube 100 may be connected to the air path interface 102. The main monitor 12 may include a pressure sensor 120 and a controller 122. The tube 100 may extend to reach the main monitor 12 and may be connected to the pressure sensor 120. The pressure sensor 120 may further be connected to the controller 122. In an embodiment, the tube 100 may be a flexible rubber tube. In other embodiments, the tube 100 may be a tube in other types, which will not be limited by the present disclosure. In another embodiment, as shown in FIG. 1, the cuff 10 may be detachably connected to the main monitor 12, such that the cuff 10 and/or the main monitor 12 may be independently replaced if required. For example, the monitor 12 may be arranged with a cuff interface 124, the tube 100 of the cuff 10 may be detachably connected with the cuff interface 124, and the tube 100 may be connected to the pressure sensor 120 through the cuff interface 124.

When the pulse diagnostic device 1 is working, the cuff 10 may contact an artery of a user. The pressure sensor 120 may sense a pressure of the gas medium in the tube 100. The pressure sensor 120 may transmit the sensed pressure of the gas medium to the controller 122. The controller 122 may obtain pulse information and blood pressure information of the user based on the pressure of the gas medium. In the present embodiment, the pressure of the gas medium may be equal to a sum of a static pressure of the cuff 10 and a pulse pressure generated by the artery of the user. The static pressure of the cuff 10 may be a pressure generated by the gas medium when the artery of the person is not pulsing. In an embodiment, the pulse diagnostic device 1 of the present disclosure may further include a digital-analog conversion circuit 1200. An end of the digital-analog conversion circuit 1200 may be connected to the pressure sensor 120, and the other end of the digital-analog conversion circuit 1200 may be connected to the controller 122. The pressure of the gas medium in the cuff 10 may be transmitted to the pressure sensor 120 through the tube 100. The pressure sensor 120 may transfer the obtained pressure of the gas medium into an analog signal and transmit the analog signal to the digital-analog conversion circuit 1200. The digital-analog conversion circuit 1200 may transfer the analog signal into a digital signal, and may transmit the digital signal to the controller 122. The controller 122 may receive the digital signal, and may analyze and process the digital signal.

In an embodiment, the pulse diagnostic device 1 may further include an inflation/deflation assembly 126. The inflation/deflation assembly 126 may be connected to the controller 122 and the tube 100. The controller 122 may control the inflation/deflation assembly 126 to inflate and/or deflate the air bag 104 to adjust the static pressure (i.e., the pressure generated by the gas medium when the artery is not pulsing) that the cuff 10 applies to the artery of the user.

In an embodiment, the inflation/deflation assembly 126 may include an air pump 1260 and a deflation valve 1262.

The air pump 1260 may be connected to the controller 122 and the tube 100. The controller 122 may initiate or stop the air pump 1260, such that the air pump 1260 may be controlled to inflate the air bag 104 or stay static. In an embodiment, as shown in FIG. 2, the pulse diagnostic device 1 may further include a first driving circuit 1264. An end of the first driving circuit 1264 may be connected to the air pump 1260, and the other end of the first driving circuit 1264 may be connected to the controller 122. The controller 122 may control the first driving circuit 1264 to further control the air pump 1260. In other embodiments, the controller 122 may initiate and stop the air pump 1260 by other means, which will not be limited by the present disclosure. For example, the air pump 1260 may be arranged with an electromagnetic valve, and the controller 122 may send a control signal to the electromagnetic valve to control the electromagnetic valve to be on and off, such that the air pump 1260 may be initiated and stopped.

The deflation valve 1262 may be connected to the controller 122 and the tube 100. The controller 122 may control the deflation valve 1262 to be on and off, such that the deflation valve 1262 is controlled to inflate or deflate the air bag 104. In an embodiment, the deflation valve 1262 of the present disclosure may be a linear deflation valve. In other embodiments, the deflation valve 1262 may be in other types, which will not be limited by the present disclosure. In still another embodiment, as shown in FIG. 2, the pulse diagnostic device 1 may further include a second driving circuit 1266. An end of the second driving circuit 1266 may be connected to the deflation valve 1262, and the other end of the second driving circuit 1266 may be connected to the controller 122. The controller 122 may control the second driving circuit 1266 to further control the deflation valve 1262. In other embodiments, the controller 122 may control the deflation valve 1262 to be on and off by other means, which will not be limited by the present disclosure. For example, the controller 122 may send a control signal to the deflation valve 1262 to control the deflation valve 1262 to be on and off.

In an embodiment, when the pulse diagnostic device 1 in the above-mentioned embodiment is working, the cuff 10 may be configured to surround an arm, a wrist, or other portions of a user, enabling the cuff 10 to contact the artery of the user. Subsequently, the controller 122 may control the inflation/deflation assembly 126 to undergo a pressure increasing process and a pressure decreasing process.

The pressure increasing process may include following operations. The controller 122 may control the air pump 1260 to initiate and control the deflation valve 1262 to be stopped. The air pump 1260 may inflate the air bag 104 of the cuff 10 through the tube 100. The pressure sensor 120 may collect the pressure of the gas medium in the tube 100, and may transfer the pressure of the gas medium to the controller 122. When the controller 122 determines that the pressure of the gas medium exceeds a predefined value, the controller 122 may control the air pump 1260 to be stopped. Alternatively, the controller 122 may perform low pass filtering to the pressure of the gas medium, a pulse pressure generated by the artery of the user may be eliminated, and the static pressure of the cuff may be obtained. When the controller 122 determines that the static pressure of the cuff exceeds a first predefined value, the controller 122 may control the air pump 1260 to stop working.

The pressure decreasing process may include following operations. The controller 122 may control the deflation valve 1262 to initiate. The air pump 1260 may not be working, and may control the gas medium in the air bag 104 to be released in a constant rate through the tube 100. In the pressure decreasing process, the constant rate of releasing the gas medium may be significant for deriving a stable pulse wave. The constant rate may enable the controller 122 to process the obtained pulse wave conveniently, and may reflect an actual pulse wave in a blood vessel, such that accuracy of the pulse wave may be obtained. In an embodiment, the constant rate may be a fixed value in a range of 0.5 mmHg/ms to 8 mmHg/ms, such as 0.5 mmHg/ms, 2 mmHg/ms, 4 mmHg/ms, 6 mmHg/ms, 8 mmHg/ms, and the like. In another embodiment, the pressure sensor 120 may include a sampling frequency (such as 60 times/second, 80 times/second, and the like). In the present disclosure, a releasing rate of the gas medium may be controlled and adjusted in a closed loop. Specifically, after the controller 122 controls the deflation valve 1262 to be on, the controller 122 may obtain a first pressure of the gas medium and a second pressure of the gas medium. The first pressure of the gas medium may be obtained by the pressure sensor 120 from a present sampling, and the second pressure of the gas medium may be obtained by the pressure sensor 120 from a previous sampling. The controller 122 may process the first pressure and the second pressure to obtain a first static pressure of the cuff and a second static pressure of the cuff correspondingly. The controller 122 may obtain an actual releasing rate of the gas medium in the air bag 104 based on the first static pressure of the cuff and the second static pressure of the cuff. When the actual releasing rate is greater than the constant rate, the controller 122 may control the deflation valve 1262 to be on in a smaller degree to reduce the releasing rate of the gas medium. When the actual releasing rate is less than the constant rate, the controller 122 may control the deflation valve 1262 to be on in a greater degree to increase the releasing rate of the gas medium.

In another embodiment, the pulse diagnostic device 1 of the present disclosure may obtain the pulse wave through the pressure increasing process and the pressure decreasing process as mentioned above. A method of obtaining the pulse wave may include following operations. The controller 122 may obtain a pulse wave of the pressure of the gas medium relative to time in the pressure increasing process and the pressure decreasing process. The controller 122 may extract a minimum value point of the pressure of the gas medium from each of various pulse periods, and a straight line between two minimum value points may be subtracted from a pulse wave between the two minimum value points, such that the pulse wave may be obtained and may serve as the pulse information.

Figure 3:
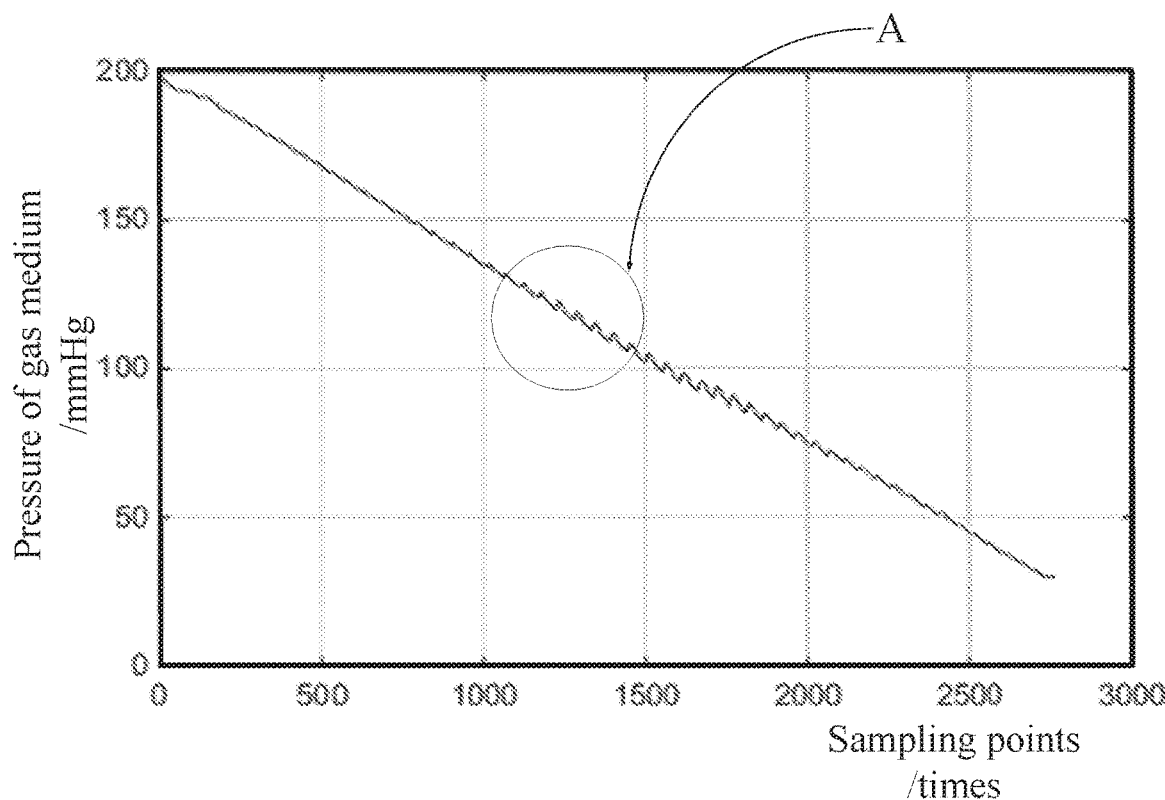
FIG. 3 is a wave diagram showing a pressure of a gas medium relative to each sampling point of a pressure sensor when the pulse diagnostic device is in a pressure decreasing process according to an embodiment of the present disclosure.
Figure 4:
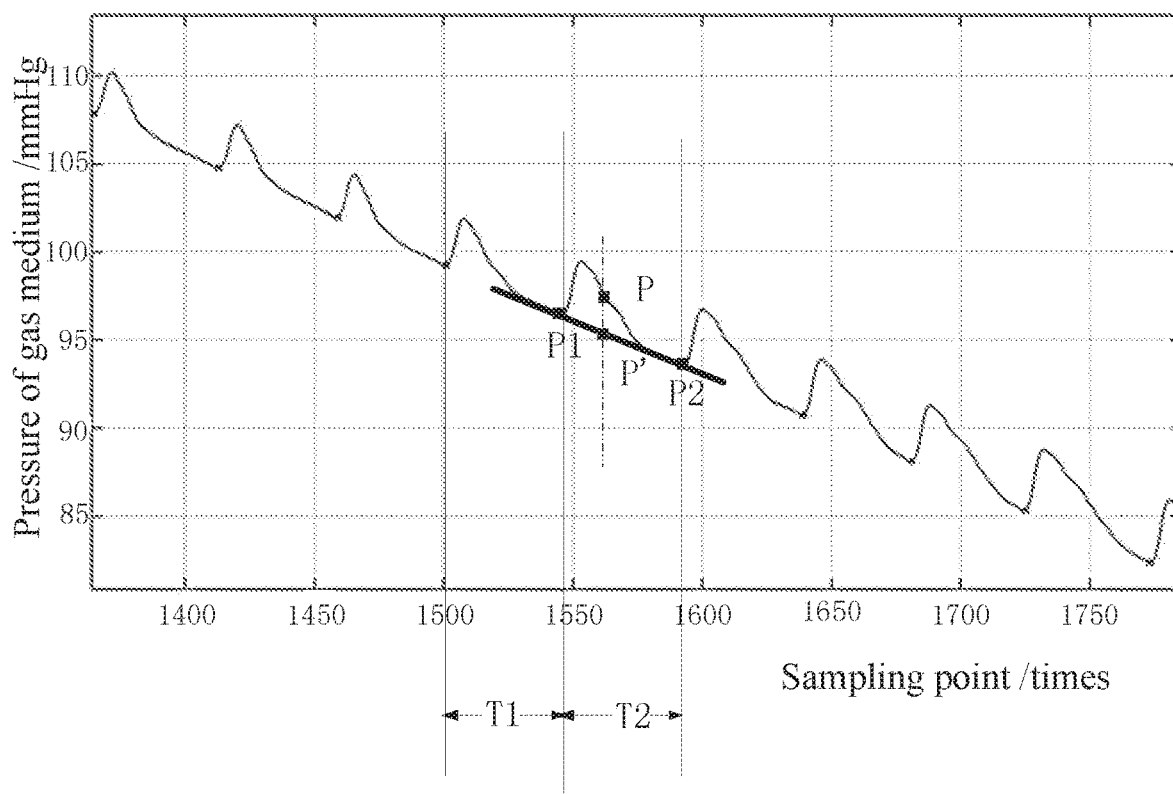
FIG. 4 is an enlarged view of a portion A shown in FIG. 3.

In an embodiment, as shown in FIG. 3 and FIG. 4, a wave diagram showing a pressure of a gas medium and each sample point of a pressure sensor when the pulse diagnostic device is reducing the pressure is shown in FIG. 3, and an enlarged view of the portion A shown in FIG. 3 is shown in FIG. 4. Horizontal axes in FIG. 3 and FIG. 4 may represent sampling points (a unit may be time(s)), and a value corresponding to a sampling point divided by a sampling frequency of the pressure sensor 120 may be time. Vertical axes in FIG. 3 and FIG. 4 may represent the pressure of the gas medium (a unit may be mmHg). The pulse may be formed by heart systole and diastole. The heart systole and diastole causes the pressure in the artery to increase and decrease. A pulse wave of a pulse period may include an ascending limb and a descending limb. A pulse period T1 and a pulse period T2 adjacent to the pulse period T1 may be taken as an example. The controller 122 may extract a minimum value point P1 of the pressure of the gas medium in the pulse period T1. The controller 122 may extract a minimum value point P2 of the pressure of the gas medium in the pulse period T2. The controller 122 may obtain an equation of a straight line between the two minimum value points P1 and P2 as: $y=k*t+b$, wherein y may be the pressure of the gas medium (in the unit of mmHg), t may be the sampling point (in the unit of time(s)), k and b may be two constants obtained based on the two minimum value points P1 and P2. The straight line between the two minimum value points P1 and P2 may be subtracted from a pulse wave between the two minimum value points P1 and P2 to obtain the pulse wave (shown as the pulse wave in FIG. 5). Specifically, a point P between the two minimum value points P1 and P2 may be taken as an example. Coordinates of the point P may be $(x_p, y_p)$, a point P' may be on the straight line and correspond to the point P, and coordinates of the point P' may be $(x_{p'}, y_{p'})$. A value of $x_p$ may be equal to a value of $x_{p'}$. On the pulse wave, coordinates of a processed P point may be $(x_p, y_p-y_{p'})$.

In another embodiment, the blood pressure information of the present disclosure may include a diastolic pressure and a systolic pressure. A method of obtaining the blood pressure information may include following operations. The controller 122 may obtain the pulse wave in the pressure increasing process as described above. The controller 122 may extract a first maximum value of the pulse wave corresponding to each pulse period, and that is, a plurality of first maximum values may be extracted from a plurality of pulse periods. A maximum of the plurality of first maximum values may be selected and determined to be a second maximum value. The controller 122 may calculate the diastolic pressure and the systolic pressure based on the second maximum value, and take the diastolic pressure and the systolic pressure as the blood pressure information. The systolic pressure may be a product value of the second maximum value and a first factor, and the diastolic pressure may be a product value of the second maximum value and a second factor. The first factor and the second factor may be referred as an amplitude factor. There may be a rule of the amplitude factor of the systolic pressure and the diastolic pressure. The amplitude factor of the systolic pressure may be in a range of 0.46 to 0.64, and the amplitude factor of the diastolic pressure may be in a range of 0.43 to 0.73.

Figure 6:
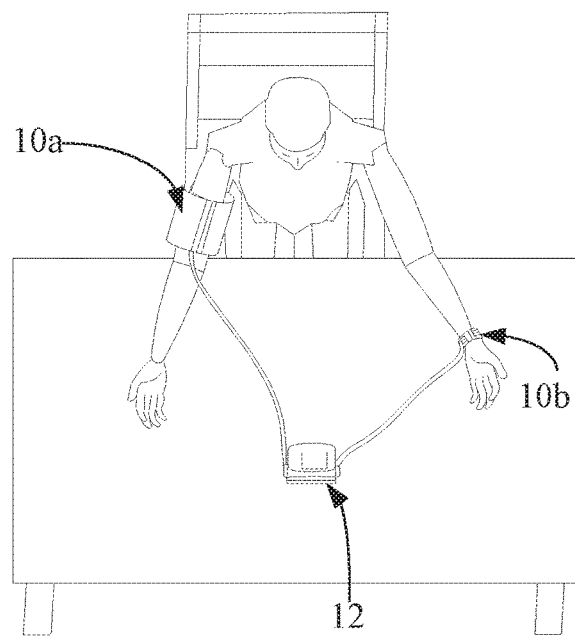
FIG. 6 is a scenario of a user using the pulse diagnostic device shown in FIG. 1 according to an embodiment of the present disclosure.

In another embodiment, referring to FIG. 1 and FIG. 2, in order to enable the pulse diagnostic device 1 to obtain the pulse information more accurately, two cuffs 10 may be configured, and the two cuffs 10 may be a first cuff 10a and a second cuff 10b. A size of the first cuff 10a may be greater than a size of the second cuff 10b. When the pulse diagnostic device 1 is working, the first cuff 10a may contact a branchial artery, and the second cuff 10b may contact a radial artery (as shown in FIG. 6). In the present embodiment, the pulse information may include a first pulse wave of the branchial artery and a second pulse wave of the radial artery. The blood pressure information may be obtained through the first pulse wave.

In an embodiment, the first pulse wave of the branchial artery and the second pulse wave of the radial artery may be similar. The first pulse wave and the second pulse wave may compensate each other, and may be comprehensively analyzed to obtain more physiological information implied by the pulse wave. Compared to collecting the pulse information from the radial artery only, more information may be obtained for reference based on the first pulse wave and the second pulse. Therefore, the controller 122 of the present disclosure may perform a similarity match between the first pulse wave and the second pulse wave, and may output a notice based on a result of the similarity match. In an embodiment, the controller 122 may predefine a similarity threshold, such as 95%, 90%, and the like. The controller 122 may perform the similarity match between the first pulse wave and the second pulse wave. When the similarity between the first pulse wave and the second pulse wave is less than the similarity threshold, a user may be noticed to re-collect the first pulse wave and the second pulse wave.

In another embodiment, as shown in FIG. 1 and FIG. 2, the pulse diagnostic device 1 may include a first cuff interface 124a and a second cuff interface 124b. The first cuff 10a may be detachably connected to the main monitor 12 through the first cuff interface 124a, and the second cuff 10b may be detachably connected to the main monitor 12 through the second cuff interface 124b. The first cuff 10a may define a first channel 100a, and the second cuff 10b may define a second channel 100b. The inflation/deflation assembly 126 of the present disclosure may further include an air path switching valve 1268. The air path switching valve 1268 may be connected to the controller 122, the air pump 1260, the deflation valve 1262, the first tube 100a of the first cuff 10a, and the second tube 100b of the second cuff 10b. The controller 122 may control the air path switching valve 1268 to be selectively connected to the first tube 100a of the first cuff 10a and the second tube 100b of the second cuff 10b. In an embodiment, the controller 122 may control the air path switching valve 1268 to connect to the tube 100a of the first cuff 10a to obtain the first pulse wave. Subsequently, the controller 122 may control the air path switching valve 1268 to connect to the tube 100b of the second cuff 10b to obtain the second pulse wave. In another embodiment, as shown in FIG. 2, the controller 122 of the present disclosure may control the air path switching valve 1268 through the third driving circuit 1261. In other embodiment, the controller 122 may send a control signal to the air path switching valve 1268, which will not be limited by the present disclosure.

In still another embodiment, the pulse diagnostic device of the present disclosure may include one cuff interface. The first cuff 10a and the second cuff 10b may be detachably connected to the main monitor 12 through the cuff interface. When the pulse diagnostic device is working, the first cuff (or the second cuff) may be connected to the main monitor through the cuff interface. The first cuff (or the second cuff) may contact the brachial artery (or the radial artery). The controller may obtain the first pulse wave (or the second pulse wave). Subsequently, the first cuff (or the second cuff) may be detached, and the second cuff (or the first cuff) may be connected to the main monitor through the cuff interface. The second cuff (or the first cuff) may contact the radial artery (or the branchial artery). The controller may obtain the second pulse wave (or the first pulse wave).

In still another embodiment, the pulse diagnostic device of the present disclosure may include a third cuff interface and a fourth cuff interface. The second cuff 10b may be detachably connected to the main monitor 12 through the fourth cuff interface. A first pressure sensor and a second pressure sensor may be arranged in an inside of the main monitor. The first pressure sensor connected to the first cuff 10a and the second pressure sensor connected to the second cuff 10b. The controller 122 may control the first cuff 10a and the second cuff 10b to work simultaneously, such that the first pulse wave and the second pulse wave may be obtained simultaneously.

As shown in FIG. 1 and FIG. 2, the main monitor 12 of the present disclosure may further include a temperature sensor 128 connected to the controller 122 (such as connected through a bus line). The temperature sensor 128 may be configured to sense a body temperature of the user. In the present embodiment, the temperature sensor 128 may be an infrared temperature sensor. In other embodiments, the temperature sensor 128 may be in other types, which will not be limited by the present disclosure.

Further referring to FIG. 1 and FIG. 2, the main monitor 12 of the present disclosure may further include a communication assembly 121 connected to the controller 122. The communication assembly 121 may be configured to transmit the pulse information and the blood pressure information processed by and obtained from the controller 122, and/or may be configured to receive an analysis result of the pulse information and the blood pressure information returned from an external terminal. In the present embodiment, the communication assembly 121 may be a Bluetooth assembly. In other embodiments, the communication assembly 121 may be in other types, which will not be limited by the present disclosure.

Figure 5:
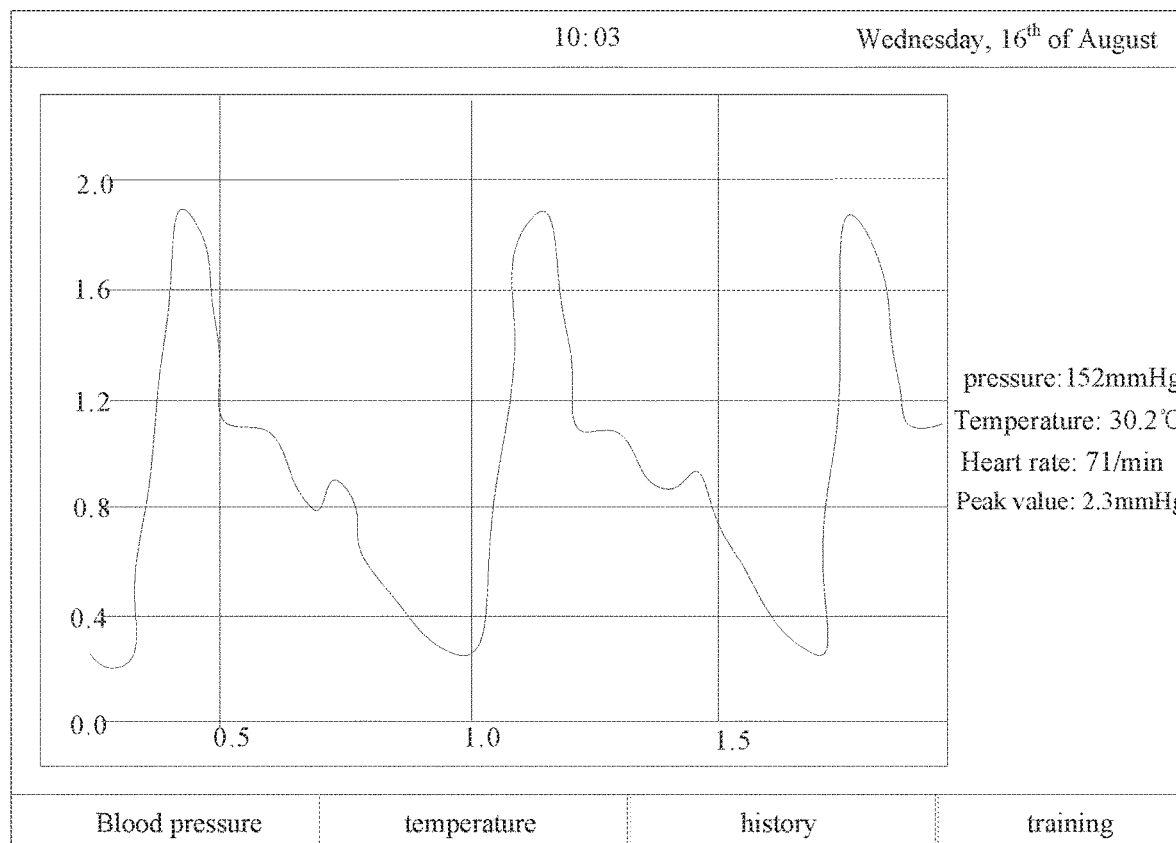
FIG. 5 is a displayed view on a display screen shown in FIG. 1 according to an embodiment of the present disclosure.

Further referring to FIG. 1 and FIG. 2, the main monitor 12 of the present disclosure may further include a display screen 123. The display screen 123 may be configured to display the pulse information and the blood pressure information (as shown in FIG. 5); and/or may be configured to display the analysis result of the pulse information and the blood pressure information returned from the external terminal. In the present embodiment, the display screen 123 may be a color liquid crystal display screen. In other embodiments, the display screen 123 may be in other types, which will not be limited by the present disclosure.

Further referring to FIG. 1 and FIG. 2, the main monitor of the present disclosure may further include components, such as an operation panel 125, a non-transitory memory 127, and the like.

Figure 7:
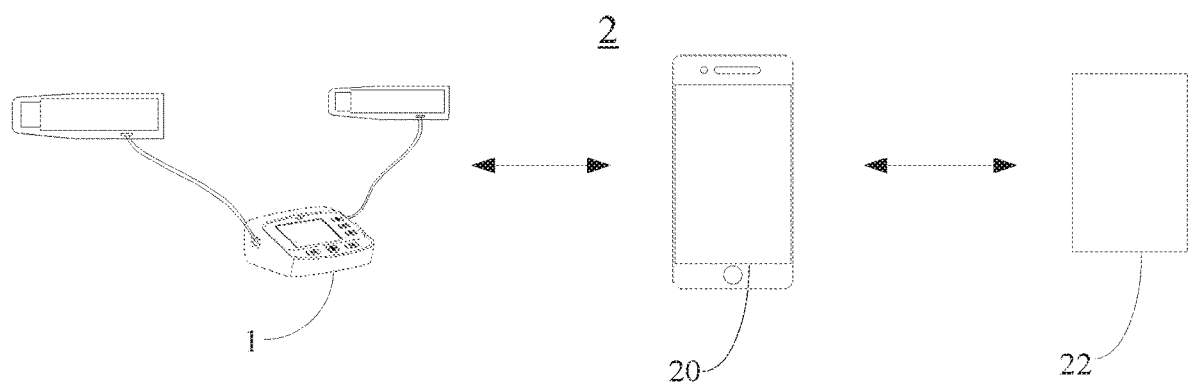
FIG. 7 is a structural schematic view of a system of pulse diagnosis according to an embodiment of the present disclosure.

As shown in FIG. 7, a structural schematic view of a system of pulse diagnosis is shown. The system 2 of pulse diagnosis may include the pulse diagnostic device 1 of any one of the above-mentioned embodiments.

In an embodiment, the system 2 of pulse diagnosis may include a mobile terminal 20 and a server 22. The mobile terminal 20 may be a mobile phone, a tablet, a computer, and the like. The mobile terminal 20 may be configured to receive the pulse information and the blood pressure information transmitted from the pulse diagnostic device 1, and may be configured to forward the pulse information and the blood pressure information. In an embodiment, the mobile terminal 20 is arranged with an application related to the pulse diagnostic device 1. The mobile terminal 20 may communicate with the pulse diagnostic device 1 by Bluetooth or by other means. The server 22 may be configured to receive the pulse information and the blood pressure information sent from the mobile terminal 20, evaluate health of the user, and return an evaluation result to the mobile terminal 20. The mobile terminal 20 may display the evaluation result or forward the evaluation result to the pulse diagnostic device 1. In another embodiment, the mobile terminal 20 may communicate with the server 22 through a wireless network, Bluetooth, or the like.

Of course, the mobile terminal 22 of the above-mentioned embodiment may be omitted. That is, the pulse diagnostic device 1 and the server 22 may communicate through Bluetooth. The server 22 may receive the pulse information and the blood pressure information sent from the pulse diagnostic device 1, evaluate the health of the user based on the pulse information and the blood pressure information, and return the evaluation result to the pulse diagnostic device 1. The pulse diagnostic device 1 may display the evaluation result.

In an embodiment, the server 22 of the above-mentioned embodiment evaluating the health of the user based on the pulse information and the blood pressure information may include following operations. The server 22 may receive the pulse information of the user, process the pulse information to eliminate noise, and compare the processed pulse information with a standard pulse wave diagram in a database, such that a pulse type corresponding to the pulse information of the user and a health condition corresponding to the pulse type may be obtained.

Figure 8:
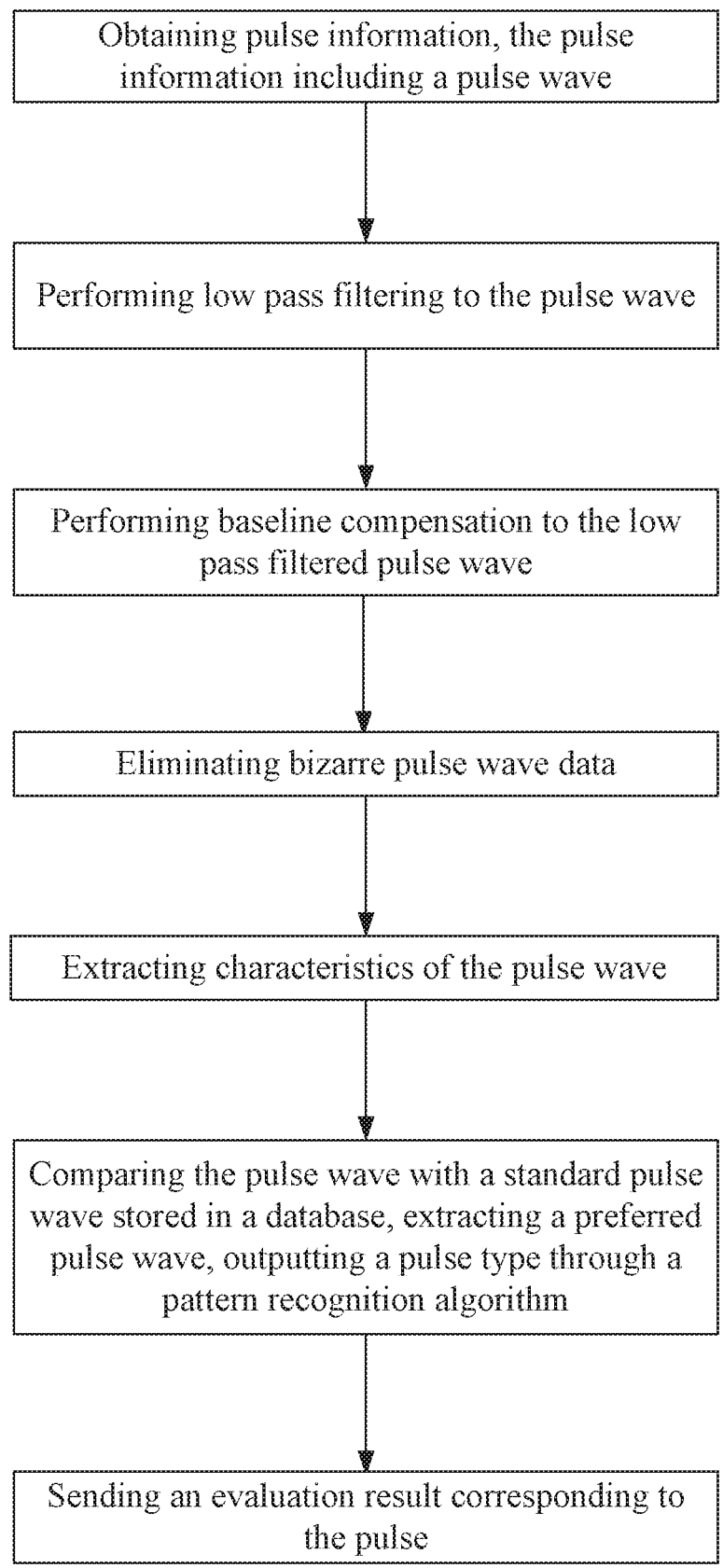
FIG. 8 is a flow chart of a server shown in FIG. 7 processing data according to an embodiment of the present disclosure.

Specifically, as shown in FIG. 8, a flow chart of a server shown in FIG. 7 processing data is shown. The server 22 may obtain the pulse information, and the pulse information may include a pulse wave. The server 22 may perform low pass filtering to the pulse wave to eliminate a bizarre noise signal. Baseline compensation may be performed to the low pass filtered pulse wave. The server 22 may eliminate bizarre pulse wave data; extract characteristics of the pulse wave; compare the pulse wave to the standard pulse wave stored in the database to extract a preferred pulse wave; output a pulse type corresponding to the extracted pulse wave through a pattern recognition algorithm; and return the evaluation result corresponding to the pulse type. The server 22 may recognize a common type of pulse, such as a normal pulse, a slippery pulse, a stringy pulse, a rapid pulse, and the like. The server 22 may store big data, and the big data may be continually updated. Therefore, the server 22 may notify the user that the user may be suffering from or would suffer from a certain disease based on the big data and the analyzed pulse type. Further, the server 22 may be flexible in optimizing and upgrading a data processing algorithm, and a database of templates of pulse waves may be upgraded at any time, such that accuracy of determining the pulse type of the user may be improved.

In summary, according to the present disclosure, the pulse diagnostic device may include the cuff and the main monitor. The main monitor may include a pressure sensor and a controller. When the pulse diagnostic device is working, the cuff may contact the artery of the user. The pressure sensor configured inside the main monitor may sense the pressure of the gas medium in the cuff, and may transmit the sensed pressure of the gas medium to the controller. The controller may obtain the pulse information and the blood pressure information based on processing the pressure of the gas medium. That is, the pulse diagnostic device of the present disclosure may obtain the pulse information and the blood pressure information. In addition, the pressure sensor is configured inside the pulse diagnostic device, whereas the pressure sensor of a conventional pulse diagnostic device is configured in the cuff. When the pressure sensor needs to be replaced, the costs of the cuff of the pulse diagnostic device may be reduced.

Further, the pulse diagnostic device of the present disclosure may further include a temperature sensor, enabling the pulse diagnostic device to have a function of collecting the body temperature.

Further, the pulse diagnostic device of the present disclosure may further include a communication assembly. The communication assembly may transmit the pulse information and the blood pressure information; and/or may receive the analysis results of the pulse information and the blood pressure information sent from the external terminal. That is, the health evaluation result corresponding to the pulse information and the blood pressure information may be analyzed and obtained by analyzing and performing statistics to the big data.

The above description illustrates embodiments of the present disclosure only, but does not limit the scope of the present disclosure. Any equivalent structural or process transformation performed based on the specification and the drawings, applied directly or indirectly in other related art, should be within the scope of the present disclosure.

What is claimed is:

1. A pulse diagnostic device, comprising:
a cuff, comprising a tube and an air bag, wherein the air bag is arranged with an air path interface, the air bag defines a chamber configured for receiving a gas medium, the tube is connected to the air path interface, and the tube defines a channel communicated with the chamber; and
a main monitor, comprising a pressure sensor and a controller, wherein the tube is connected to the pressure sensor, and the pressure sensor is further connected to the controller,
wherein the cuff is configured to encircle an arm or a wrist of a user to encircle an artery of the user, the pressure sensor is configured to sense a pressure of the gas medium in the tube to obtain a sensed pressure of the gas medium, the pressure sensor is configured to transmit the sensed pressure of the gas medium to the controller, and the controller is configured to obtain pulse information and blood pressure information of the user based on the pressure of the gas medium; and
the pulse diagnostic device is configured to perform a pressure increasing process and a pressure decreasing process, the pressure of the gas medium is a sum of a static pressure of the cuff and a pulse pressure generated by the artery, and in the decreasing process, the controller is configured to perform operations of:
controlling a deflation valve to be switched on;
obtaining a first pressure and a second pressure, wherein the first pressure is obtained by the pressure sensor from a present sampling, the second pressure is obtained by the pressure sensor from a previous sampling;
processing the first pressure and the second pressure to obtain a first static pressure of the cuff and a second static pressure of the cuff;
obtaining an actual releasing rate of the gas medium in the air bag based on the first static pressure of the cuff and the second static pressure of the cuff;

controlling the deflation valve to be on in a smaller degree when the actual releasing rate is greater than a constant rate, such that the actual releasing rate of the gas medium is reduced; and controlling the deflation valve to be on in a greater degree when the actual releasing rate is less than the constant rate, such that the actual releasing rate of the gas medium is increased;

the pulse diagnostic device further comprises an inflation/deflation assembly, connected to the controller and the tube, wherein the controller is configured to control the inflation/deflation assembly to inflate and/or deflate the air bag to adjust the static pressure applied by the cuff onto the artery of the user; the inflation/deflation assembly comprises:

an air pump, connected to the controller and the tube, wherein the controller is configured to control the air pump to initiate or stop, such that the air pump is configured to be controlled to inflate or stop inflating the air bag; and the deflation valve, connected to the controller and the tube, wherein the controller is configured to control the deflation valve to be on and off, such that the deflation valve is configured to be controlled to release or stop releasing the gas medium from the air bag;

in the pressure increasing process, the controller is configured to control the air pump to initiate, the air pump is configured to inflate the air bag through the tube, the controller is configured to control the air pump to stop inflating when the pressure of the gas medium exceeds a predefined value;

in the pressure decreasing process, the controller is configured to control the deflation valve to be switched on, and to control the gas medium in the air bag to be released in the constant rate through the tube; and the controller is configured to perforin operations of:

obtaining a third pulse wave of the pressure of the gas medium relative to time in the pressure increasing process and a fourth pulse wave of the pressure of the gas medium relative to time in the pressure decreasing process, wherein the pressure decreasing process comprises a plurality of pulse periods;

extracting a minimum value point of the pressure of the gas medium from each of the plurality of pulse periods, to obtain a plurality of minimum value points; and subtracting signals below a straight line between two of the plurality of minimum value points from a fifth pulse wave between the two minimum value points to obtain a sixth pulse wave serving as the pulse information.

2. The pulse diagnostic device according to claim 1, wherein the constant rate is a fixed value in a range of 0.5 mmHg/second to 8 mmHg/second.

3. The pulse diagnostic device according to claim 1, wherein the controller is further configured to perform operations of:

obtaining the third pulse wave of the pressure of the gas medium relative to time in the pressure increasing process;

extracting a first maximum value of the pressure of the gas medium from each of the plurality of pulse periods, wherein a plurality of first maximum values are extracted;

determining a second maximum value from the plurality of first maximum values, wherein the second maximum value is a greatest value of the plurality of first maximum values; and calculating a systolic pressure and a diastolic pressure based on the second maximum value, taking the systolic pressure and the diastolic pressure as the blood pressure information, wherein the systolic pressure is equal to a product value of the second maximum value and a first factor, and the diastolic pressure is equal to a product value of the second maximum value and a second factor.

4. The pulse diagnostic device according to claim 1, wherein the cuff comprises a first cuff and a second cuff, a size of the first cuff is greater than a size of the second cuff; and the first cuff is configured to encircle the arm or the wrist of the user to encircle a branchial artery, and the second cuff is configured to encircle the arm or the wrist of the user to encircle a radial artery.

5. The pulse diagnostic device according to claim 4, wherein the inflation/deflation assembly further comprises an air path switching valve connected to the controller, the air pump, the deflation valve, a first tube of the first cuff and a second tube of the second cuff; and the controller is configured to control the air path switching valve to connect to the first tube of the first cuff or the second tube of the second cuff.

6. The pulse diagnostic device according to claim 5, wherein the pulse information comprises a first pulse wave of the branchial artery and a second pulse wave of the radial artery, and the controller is configured to perform operations of:

controlling the air path switching valve to connect to the first tube of the first cuff to obtain the first pulse wave; and controlling the air path switching valve to connect to the second tube of the second cuff to obtain the second pulse wave.

7. The pulse diagnostic device according to claim 6, wherein the controller is further configured to perform a similarity match between the first pulse wave and the second pulse wave, and output notice information based on a result of the similarity match.

8. The pulse diagnostic device according to claim 1, wherein the main monitor further comprises a temperature sensor connected to the controller and configured to sense a body temperature.

9. The pulse diagnostic device according to claim 1, wherein the main monitor further comprises a communication assembly, and the communication assembly is connected to the controller and is configured to perform operations of:

transmitting the pulse information and the blood pressure information to an external terminal; and/or receiving an analysis result of the pulse information and the blood pressure information sent from the external terminal.

10. The pulse diagnostic device according to claim 1, wherein the main monitor further comprises a display screen configured to:

display the pulse information and the blood pressure information; and/or display an analysis result of the pulse information and the blood pressure information.

11. The pulse diagnostic device according to claim 1, further comprising:
a first driving circuit comprising two ends, wherein an end of the first driving circuit is connected to the air pump, and the other end of the first driving circuit is connected to the controller; and/or
a second driving circuit comprising two ends, wherein an end of the second driving circuit is connected to the deflation valve, and the other end of the second driving circuit is connected to the controller; and/or
a digital-analog conversion circuit comprising two ends, wherein an end of the digital-analog conversion circuit is connected to the pressure sensor, and the other end of the digital-analog conversion circuit is connected to the controller, the pressure sensor is configured to convert the pressure of the gas medium into an analog signal, and the digital-analog conversion circuit is configured to convert the analog signal into a digital signal.

12. A system of pulse diagnosis, comprising: a pulse diagnostic device and a server, wherein the pulse diagnostic device comprises:
a cuff, comprising a tube and an air bag, wherein the air bag is arranged with an air path interface, the air bag defines a chamber capable of receiving a gas medium, the tube is connected to the air path interface, and the tube defines a channel communicating with the chamber of the air bag;
a main monitor, comprising a pressure sensor and a controller, wherein the tube extends to reach the main monitor and is connected to the pressure sensor, the pressure sensor is further connected to the controller; and
a communication assembly,
wherein the cuff is configured to encircle an arm or a wrist of a user to encircle an artery of the user; the pressure sensor is configured to sense a pressure of the gas medium in the tube and transmit the sensed pressure of the gas medium to the controller; the controller is configured to obtain pulse information and blood pressure information of the user based on the pressure of the gas medium; the communication assembly is configured to transmit the pulse information and blood pressure information to the server; the server is configured to receive the pulse information and the blood pressure information, evaluate health of the user based on the pulse information and the blood pressure information, and send an evaluation result to the pulse diagnostic device; and the pulse diagnostic device is configured to display the evaluation result; and
the pulse diagnostic device is configured to perform a pressure increasing process and a pressure decreasing process, the pressure of the gas medium is a sum of a static pressure of the cuff and a pulse pressure generated by the artery, and in the decreasing process, the controller is configured to perform operations of:
controlling a deflation valve to be switched on;
obtaining a first pressure and a second pressure, wherein the first pressure is obtained by the pressure sensor from a present sampling, the second pressure is obtained by the pressure sensor from a previous sampling;
processing the first pressure and the second pressure to obtain a first static pressure of the cuff and a second static pressure of the cuff;
obtaining an actual releasing rate of the gas medium in the air bag based on the first static pressure of the cuff and the second static pressure of the cuff;
controlling the deflation valve to be on in a smaller degree when the actual releasing rate is greater than a constant rate, such that the actual releasing rate of the gas medium is reduced; and
controlling the deflation valve to be on in a greater degree when the actual releasing rate is less than the constant rate, such that the actual releasing rate of the gas medium is increased; the pulse diagnostic device further comprises an inflation/deflation assembly connected to the controller and the tube, wherein the controller is configured to control the inflation/deflation assembly to inflate and/or deflate the air bag to adjust the static pressure applied b r the cuff onto the artery of the user; and the inflation/deflation assembly comprises:
an air pump, connected to the controller and the tube, wherein the controller is configured to control the air pump to initiate or stop, such that the air pump is configured to be controlled to inflate or stop inflating the air bag; and
the deflation valve, connected to the controller and the tube, wherein the controller is configured to control the deflation valve to be on and off, such that the deflation valve is configured to be controlled to release or stop releasing the gas medium from the air bag;
in the pressure increasing process, the controller is configured to control the air pump to initiate, the air pump is configured to inflate the air bag through the tube, the controller is configured to control the air pump to stop inflating when the pressure of the gas medium exceeds a predefined value; and
in the pressure decreasing process, the controller is configured to control the deflation valve to be switched on, and to control the gas medium in the air bag to be released in the constant rate through the tube; and
the controller is configured to perform operations of:
obtaining a third pulse wave of the pressure of the gas medium relative to time in the pressure increasing process and a fourth pulse wave of the pressure of the gas medium relative to time in the pressure decreasing process, wherein the pressure decreasing process comprises a plurality of pulse periods;
extracting a minimum value point of the pressure of the gas medium from each of the plurality of pulse periods, to obtain a plurality of minimum value points; and
subtracting signals below a straight line between two of the plurality of minimum value points from a fifth pulse wave between the two minimum value points to obtain a sixth pulse wave serving as the pulse information.

13. The system of pulse diagnosis according to claim 12, wherein the controller is further configured to perform operations of:
obtaining the third pulse wave of the pressure of the gas medium relative to time in the pressure increasing process;
extracting a first maximum value of the pressure of the gas medium from each of the plurality of pulse periods, wherein a plurality of first maximum values are extracted;
determining a second maximum value from the plurality of first maximum values, wherein the second maximum value is a greatest value of the plurality of first maximum values; and calculating a systolic pressure and a diastolic pressure based on the second maximum value, taking the systolic pressure and the diastolic pressure as the blood pressure information, wherein the systolic pressure is equal to a product value of the second maximum value and a first factor, and the diastolic pressure is equal to a product value of the second maximum value and a second factor.

* * * * *